United States Patent [19]

Stone

[11] Patent Number: 5,184,603
[45] Date of Patent: Feb. 9, 1993

[54] AUTOMATIC INTUBATING LARYNGOSCOPE

[76] Inventor: J. Gilbert Stone, 25 Bank St., New York, N.Y. 10014

[21] Appl. No.: 656,961

[22] Filed: Feb. 15, 1991

[51] Int. Cl.⁵ ............................................. A61B 1/06
[52] U.S. Cl. .................................................... 128/11
[58] Field of Search ...................... 128/10, 11, 12, 13, 128/16, 200.26

[56] References Cited

U.S. PATENT DOCUMENTS

| | | | |
|---|---|---|---|
| 4,337,761 | 7/1982 | Upsher | 128/11 |
| 4,527,553 | 7/1985 | Upsher | 128/11 |
| 4,583,527 | 4/1986 | Musicant et al. | 128/11 |

Primary Examiner—Robert P. Swiatek

[57] ABSTRACT

An intubating instrument comprising a laryngoscopic blade having a rounded distal end adapted for introduction into a patient's throat to expose the laryngeal opening for endotracheal intubation; side walls formed integrally with the blade and forming an elongated channel for an endotracheal tube; the channel being adapted to retain the tube within the laryngoscopic blade during insertion and manipulation of the instrument and to accommodate forward displacement of the tube beyond the distal end; the blade having a proximal end having a first quick-connect coupling associated therewith; a support handle housing for supporting the blade; a second quick-connect coupling matable with the first quick-connect coupling disposed at the lowermost portion of the support handle housing; the first and second quick-connect couplings being adapted to be mechanically engaged to lock the blade to the handle housing in a predetermined angular relationship; an endotracheal tube driver mounted in the handle housing; a tube driver operatively associated with the handle housing and the blade and adapted to engage a proximal portion of an endotracheal tube in the channel and to advance the tube beyond the distal end of the blade to introduce the distal end of the tube into the trechea; a finger-activated trigger mounted on the handle housing and adapted to initiate operation of the tube driver, whereby the exposure of the glottic opening and the introduction of the endotracheal tube may be effected with one hand while holding the handle housing.

9 Claims, 3 Drawing Sheets

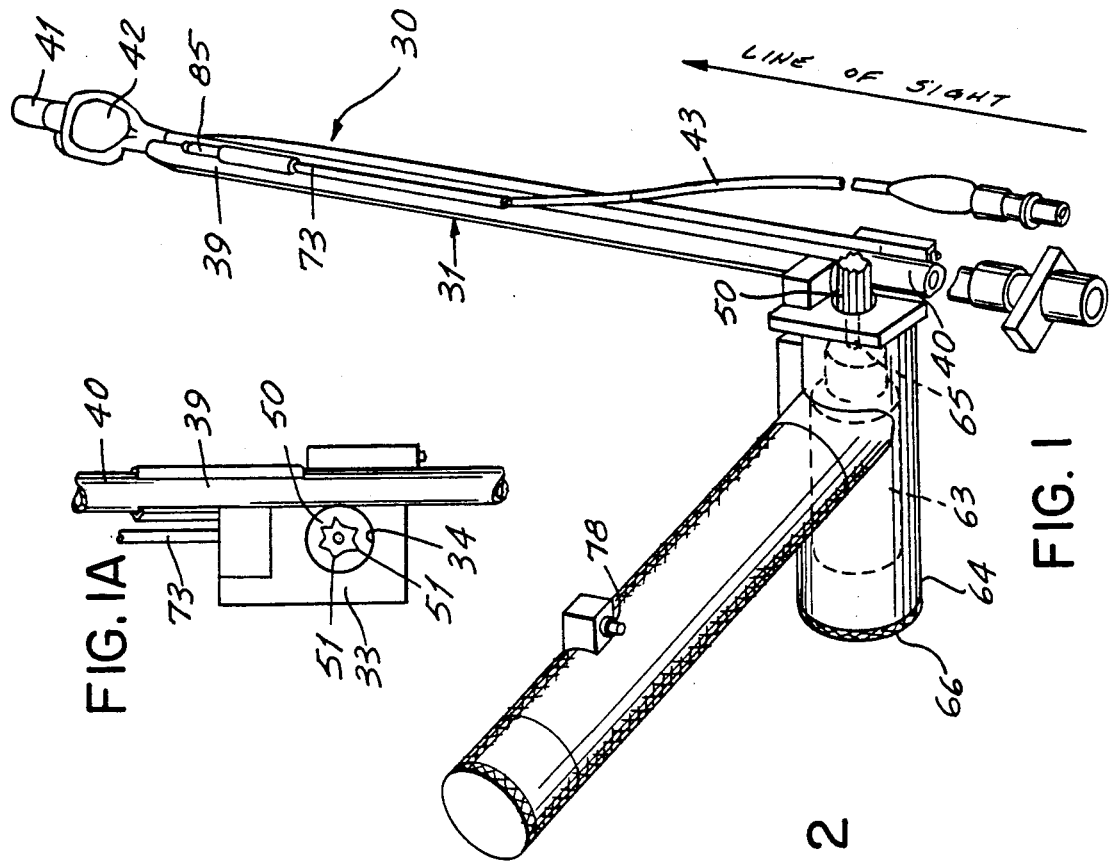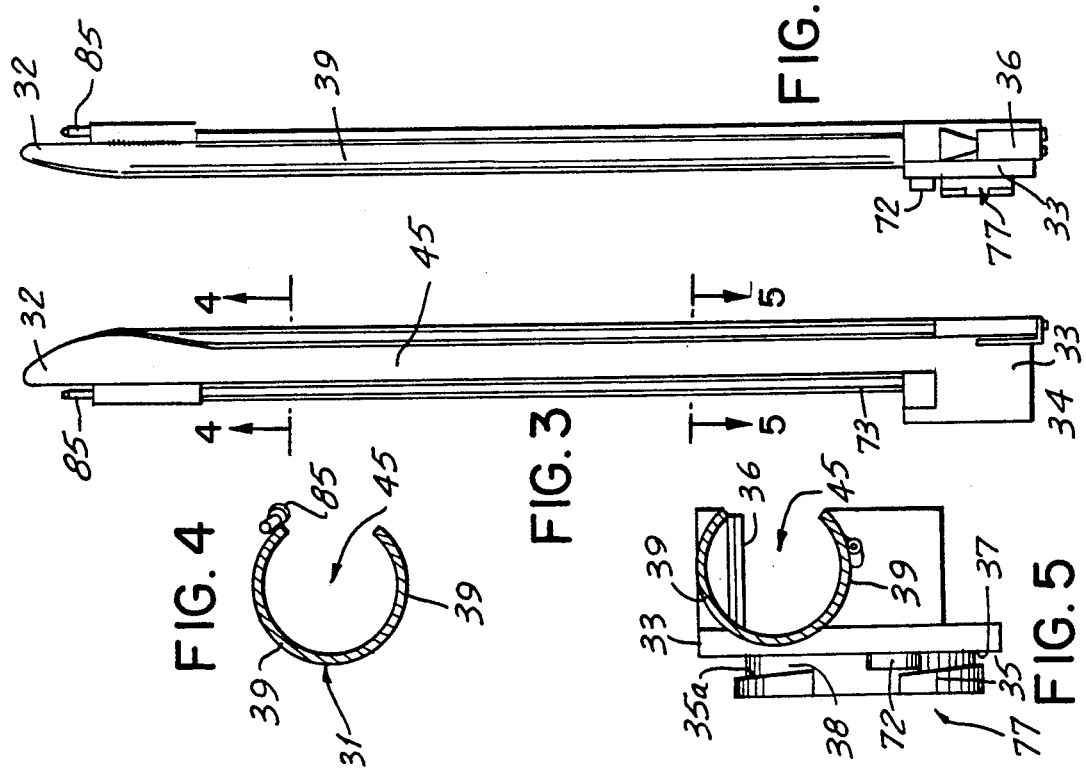

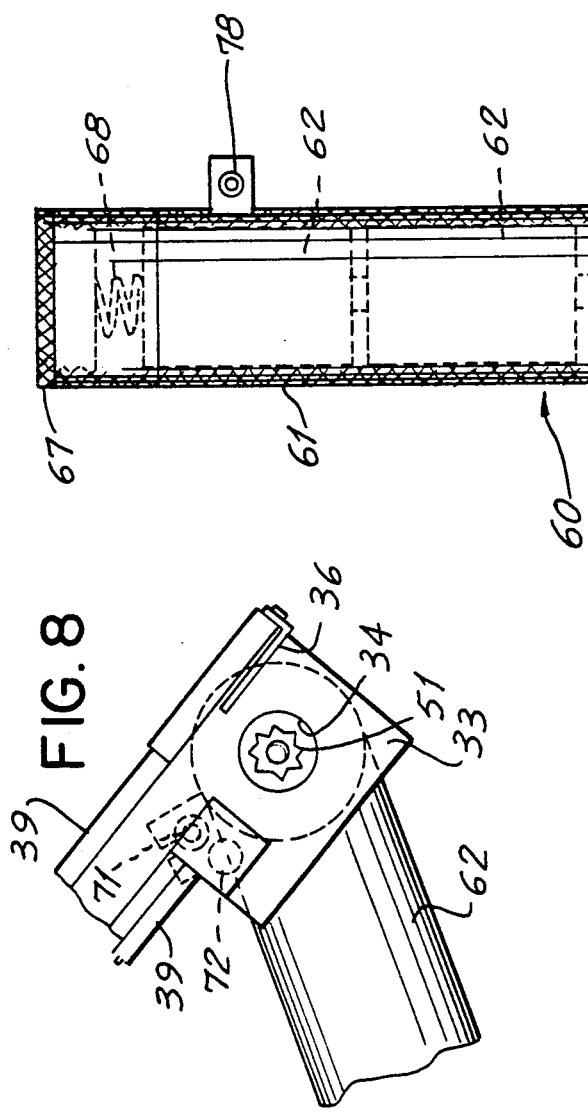
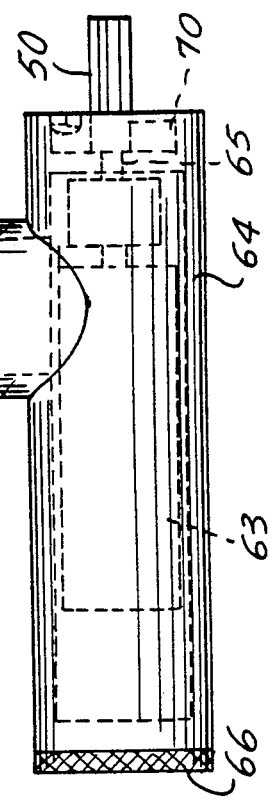
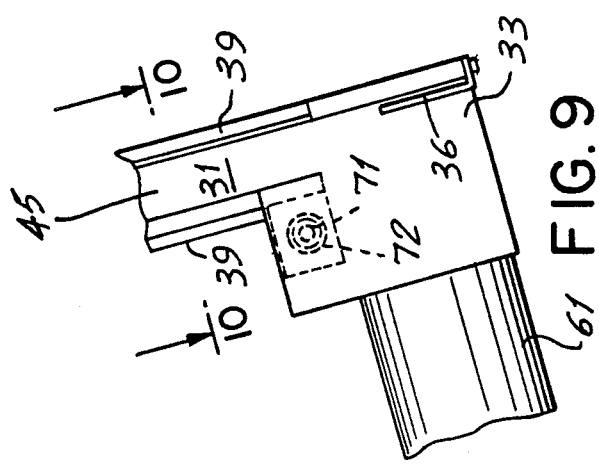
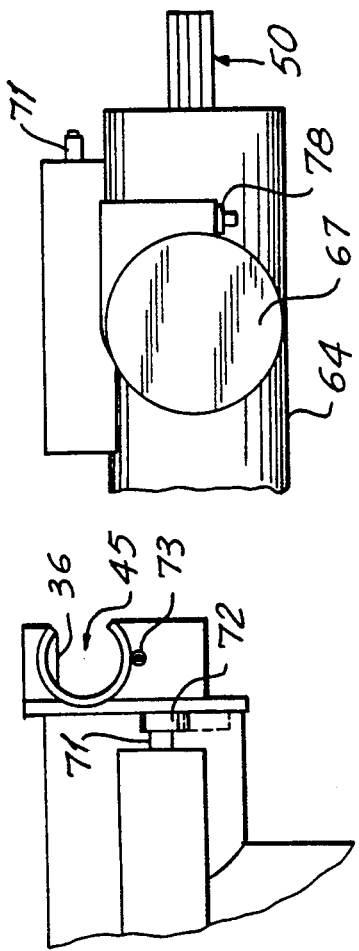

AUTOMATIC INTUBATING LARYNGOSCOPE

BACKGROUND OF THE INVENTION

The application of assisted or "artificial respiration" is an absolute lifesaving necessity when breathing ability is compromised or otherwise interfered with by coma, drug-induced depression, or acute pulmonary disease. Under these life-threatening conditions and during anesthesia, patients are ventilated by mechanical respirators which inflate the lungs. Oxygen is delivered to the lungs through a flexible plastic conduit (endotracheal tube), which connects the respirator the windpipe. The oropharyngeal passage is curved and narrow, and the vocal cords and glottic opening often cannot be seen even with a tongue depressor. Specifically, the relationship of the epiglottis to the glottic opening is such that during endotracheal intubation it is necessary to move the epiglottis to expose the glottic opening. The insertion of an endotracheal tube is a difficult and often dangerous procedure which requires the use of an instrument called a laryngoscope. The procedure in which a laryngoscope is used by a physician to manipulate the tongue and the epiglottis to expose the glottis for visualization and subsequent manual insertion of an endotracheal tube is called endotracheal intubation.

A conventional laryngoscope is an optical instrument having a rigid blade and a focused light source adapted to illuminate the region immediately beyond the blade tip. During laryngoscopy the patient is supine with the neck fully extended and the top of the head at the edge of the support surface. The laryngoscopist stands over the patient viewing the face as the tip of the blade is passed into the pharynx. Gentle upward traction is applied to the base of the tongue to lift it off the posterior surface of the pharynx and to expose the vocal cords and glottic opening. Thereafter, endotracheal intubation may be manually effected. More specifically, with the oropharyngeal passage clearly viewed with laryngoscopic techniques, the endotracheal tube may be inserted by grasping its proximal end and pushing it along side the laryngoscope blade into the trachea.

Typically, during intubation, the left hand of the doctor manipulates the laryngoscope and the right hand carefully threads the endotracheal tube through the oropharynx, passing the tube between the vocal cords and into the larynx and trachea. Anatomically, individual oropharyngeal channels vary greatly from patient to patient in size, shape and distensibility. Direct visualization is often difficult, and indeed in many cases the requisite exposure cannot be obtained by the laryngoscopist alone without assistance of another person who manipulates the larynx by the application of external pressure on the neck over the Adam's Apple. On occasion, the glottic opening may be viewed, but the laryngoscopist cannot maneuver the long (approximately 12 inches) plastic endotracheal tube through the narrow, curved and often quite still anatomical path.

Over the years lighted laryngoscopic blades have evolved into a myriad shapes and forms in an attempt to facilitate endotracheal intubation. Representative of the state of art are U. S. Pat. Nos. 4,793,327 for ENDOTRACHEAL INTUBATION DEVICE; 4,825,858 for AUTOMATIC INTUBATION DEVICE FOR GUIDING ENDOTRACHEAL TUBE INTO TRACHEA; 4,827,910 for LARYNGOSCOPE; 4,850,340 for ENDOTRACHEAL TUBE APPARATUS AND METHOD; 4,838,245 for INSTRUMENT FOR THE INSERTION OF ANESTHETIC CATHETERS; 4,884,558 for LARYNGOSCOPE ASSEMBLY INCLUDING DISPOSABLE PROTECTIVE ENCLOSURE; 4,905,669 for LARYNGOSCOPE; 4,947,829 for MODULAR BLADE LARYNGOSCOPE; and 4,947,896 for LARYNGOSCOPE. Despite the evolution of specialized instrumentation and advanced techniques, endotracheal intubation always requires considerable skill, often requires two persons, and on occasion cannot even be accomplished.

SUMMARY OF THE INVENTION

The present invention is directed to a new and improved method and and newly developed medical instrument, and automatic intubating laryngoscope, specifically designed to facilitate endotracheal intubation. The new instrument includes a special power handle and a generally perpendicular cantilevered lighted laryngoscopic blade for illuminating and dilating the upper airway passages. In accordance with the invention, the blade itself is in the form of a channel into which a plastic endotracheal tube is pre-loaded. The power handle includes a DC source and a miniaturized electric motor with a projecting toothed drive shaft. As will be understood, when the laryngoscopic blade itself is inserted in the oropharynx, the distal tip of the pre-loaded endotracheal tube is positioned adjacent to the glottic opening. In accordance with the invention and as an important feature of the new instrument, a trigger-activated driving or feeding mechanism is associated with the proximal portion of the laryngoscopic blade and engages proximal portions of the endotracheal tube. The distal end of the tube is advanced automatically into the trachea by activating the driving mechanism, advantageously by a simple pushbutton switch on the power handle. As an important aspect of the invention, the laryngoscope-intubation instrument is configured so that only one hand is needed to operate it, leaving the other hand free to adjust the position of the larynx for optimal glottic exposure. Moreover, the new instrument, which provides direct glottic vision, is sufficiently small, light weight, and compact to fit easily into the coat pocket of a physician or other trained medical person who performs endotracheal intubation, often in an emergency.

Specifically, the new automatic laryngoscope blade tip slopes upward slightly and tapers to a blunt rounded end. During intubation, gentle upward pressure is applied and the tip of the blade is passed under the epiglottis exposing the vocal cords. The right hand is free to assist with and improve glottic exposure by external manipulation of the larynx. Once in position, the pushbutton on the instrument handle is squeezed by the left hand causing the motor to be energized and the endotracheal tube to be driven out past the top of the blade and into the trachea. When the tube been advanced (approximately two inches) down the trachea and into its operative respirating position, the proximal end of the endotracheal tube is grasped and the new intubating laryngoscope instrument is retracted from the patient.

The new intubating laryngoscope blade, which is adapted to "quick-connect" by a bayonet mounting to the power handle, includes a light source which is energized by the power handle. Light emanates from the lamp disposed at the tip of the upper surface of the laryngoscope (as it is held in the mouth), and the mouth, pharynx, larynx and upper treahea are illuminated during insertion of the blade as is common in all laryngoscopic procedures.

For a more complete understanding of the method and apparatus of the present invention and a better appreciation of the attendant advantages of the new intubation technology represented thereby, reference should be made to the following detailed description taken in conjunction with the accompanying drawings.

DETAILED DESCRIPTION OF THE DRAWING

FIG. 1 is a perspective view of a new and improved intubating laryngoscope embodying the principles of the present invention;

FIG. 1A is a fragmentary top plan view of a preferred embodiment of a toothed drive mechanism of the present invention;

FIG. 2 is a side elevational view of a laryngoscope blade/endotracheal tube channel of the present invention;

FIG. 3 is a top plan view of the blade/tube channel of FIG. 2;

FIG. 4 is an enlarged cross-section view taken along line 4—4 of FIG. 3;

FIG. 5 is an enlarged cross-sectional view taken along line 5—5 of FIG. 3;

FIG. 6 is a side elevational view of the power handle of the intubating laryngoscope of the present invention;

FIG. 7 is a bottom end view of the mechanism of FIG. 6;

FIG. 8 is a fragmentary side elevational view showing the attachment of the blade/endotracheal tube channel to the power handle in accordance with the principles of the present invention;

FIG. 9 is a fragmentary end view of the connected blade/endotracheal tube channel showing the completion of the optical illumination system;

FIG. 10 is a fragmentary cross-section view taken along line 10—10 of FIG. 9;

DETAILED DESCRIPTION OF THE INVENTION

Figure 11:
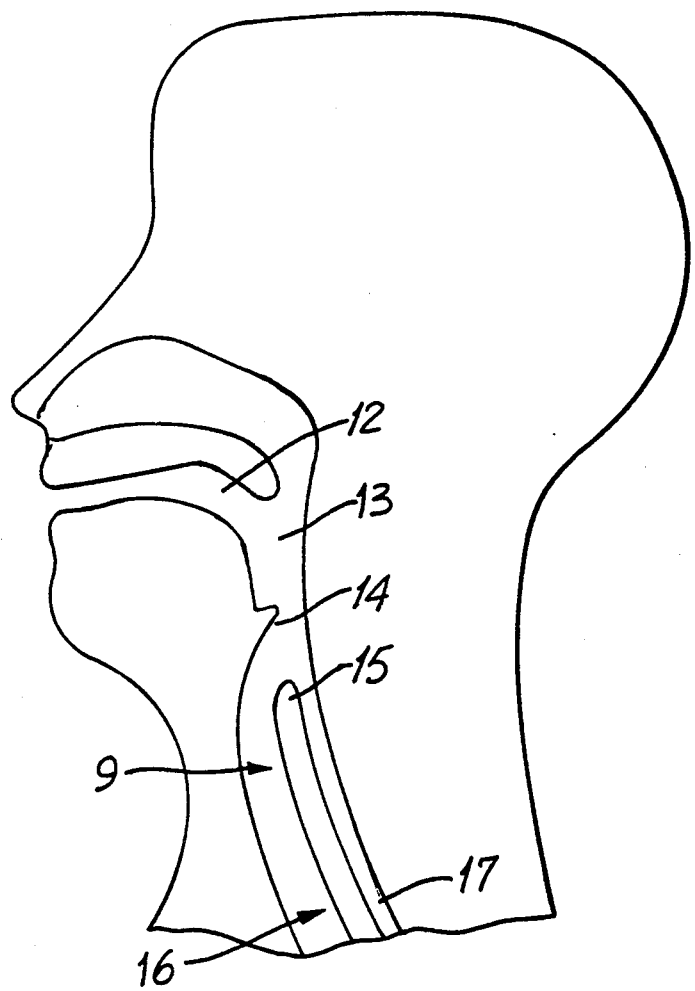
FIG. 11 is a schematic view of the cross-section of a patient's head.
Figure 12:
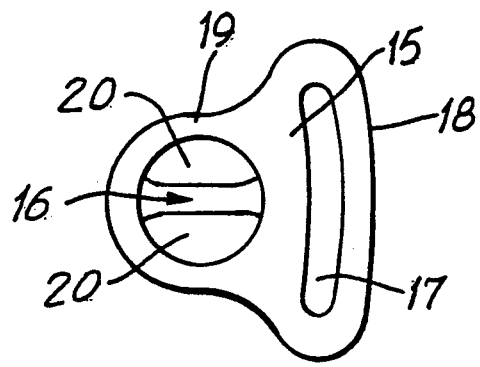
FIG. 12 is a cross-sectional view of the neck at the level of the vocal cords showings the larynx, vocal cords, and the esophagus.

Initially referring to FIG. 11, the curved and narrow oropharyngeal passage of a a patient to be intubated is illustrated in a side elevational view. To that end, it is the objective of the physician performing intubation to pass an endotracheal tube into the trachea 16 through the mouth 12 into the pharynx 13 and past the epiglottis 14 immediately above the corniculus 15, which separates the trachea 16 from the esophagus 17. It will be appreciated that this task requires considerable care and great skill. As shown in FIG. 12, the esophagus has a cross-section which is essentially oblong and defined by the esophageal wall 18. The larynx 9 has cartilagenous ring 19 and two vocal cords 20, as shown. It is the objective of the physician/anesthetist to place an endotracheal tube through the larynx 9 and into the trachea 16 is quickly and non-traumatively as possible.

Referring now to FIG. 1, the new and improved intubating laryngoscope of the present invention is generally indicated by reference numeral 30 and comprises and elongated laryngoscopic blade 31 with integral side walls 39 of generally curved cross-section, giving the blade 31 a generally semi-cylindrical appearance and forming a channel 45 for an endotracheal tube 40.

Referring to FIG. 2 and FIG. 3, the blade 31 has a generally rounded distal end 32, which is adapted to be manipulated in the patient's throat to expose the glottic opening to enable an endotracheal tube 40 carried by the channel 45 to be inserted in the trachea, as will be described in great detail hereinafter. The curved cross-section of the channel 45 is illustrated in FIG. 4, looking towards the distal end 32 of the blade 31. The blade 31 is mounted to a power handle 60 through a plate 33 to which the blade is secured.

As is conventional with laryngoscope blades, a high intensity lamp 85 is supported adjacent to tip 32 for illumination of the mouth and the airway passages leading to the trachea. At the proximal end of the blade 31, a flatspring 36 is cantilevered from a vertical wall 73, projecting from the mounting plate 33 in a manner to provide bias of the endotracheal tube 40 towards an opening 34 formed in the plate. As shown in FIG. 1A, a tube-engaging cogwheel 50 projects through the opening 34, so as to contact the endotracheal tubing. The engagement of the tube through the driving cogwheel 50 is enhanced and ensured by the bias of the flatspring 36 as will be understood.

In accordance with the principles of the invention, a special T-shaped power handle 60 is provided for powering the driving cog 50 and for energizing the lamp 85. More particularly as shown in FIG. 6, the handle 60 includes a cylindrical leg 61, which houses a series of DC dry cells 62 which are appropriately wired to a miniaturized DC electric motor 63 housed in an intersecting cylindrical casing 64, which is connected to the cylindrical housing 61. The electrical motor 63 has a drive shaft 65, which is directly connected to the toothed cogwheel 50, as shown. Access to the motor 63 and housing 64 is obtained through a threaded circular end cap 66. Similarly, access to and replacement of the batteries 62 may be had through circular threaded end cap 67, which has a biasing coil spring 68 urging the series of batteries 62 into operative contact with one another.

As a very important aspect of the present invention, the motor 63 is operated by a pushbutton switch 78 mounted at the upper external portion of the housing 61, where it may be readily accessed by the user of the new instrument. While the specific wiring and circuits are not shown, depression of the pushbutton 78 energizes the motor 63 to rotate the cogwheel 50 in a counter-clockwise direction, as viewed in FIG. 1. The rotation of the cogwheel 50 will advance the endotracheal tube 40 forwardly through the channel 45 of the blade 31 to project the distal end 41 of the endotracheal tube into the trachea. When the tube 40 is thus positioned, a balloon seal 42 may be inflated through an inflation tube 43 in known fashion to maintain an air-tight seal in the trachea about the end 41 of the endotracheal tube.

The blade 31 itself is adapted to be quickly connected and disconnected from the T-shaped handle 60 for the purposes of autoclaving or sterilizing the blade. To that end, a special first bayonet "quick-connect" member 77 is included on the lower surfaces of the plate 33. A series of lugs 35, having tapered surfaces 35a and separated from the undersurface 37 of the plate 33 by a groove 38 constitute the first bayonet member 77 which is adapted to be inserted into corresponding but reversed second bayonet locking member 70 formed at the open end of the casing 64 (FIG. 6) concentrically with the shaft 65. Thus when the plate 33 adjacent proximal end of the blade 31 is placed over the cogwheel 50 through the opening 34, the lungs 35 may be inserted into the corresponding second bayonet locking member 70 formed integrally at the upper end of casing 64. When the blade 31 is rotated into locking position, the lugs 35 on the bottom side of the plate engage and lock in juxtaposition with the correspondingly and matingly shaped lugs formed in the housing 64 and indicated generally by the reference numeral 70 (FIG. 6). As shown in FIG. 8, as the blade 31 is locked in its imperative position, a spring loaded electrical contact 71 carried on the handle assembly (FIG. 7) engages a contact 72 (FIG. 2) which is electrically connected through an insulated conductor 73 to the lamp 34 at the distal end of the blade.

The new instrument may be used by an anesthesiologist or other trained medical person to expose the larynx and to automatically insert an endotracheal tube 40. With the blade 31 assembled to the power handle 60 the lamp 34 will be lighted. Thereafter, an endotracheal tube 40 is loaded into the channel 45 with its distal tip 41 generally coincident with the distal tip 32 of the blade 31.

The laryngoscopic blade may be held through the handle in one hand and the blade may be manipulated by the operator to expose the laryngeal opening. If the larynx does not come easily into view, the operator has another hand free to improve exposure by repositioning the patient's larynx.

In accordance with a most important aspect of the invention, at the moment the laryngeal opening is visualized and the tip of the laryngoscopic blade 32 is proximate thereto, the tip of the endotracheal tube is automatically fed or delivered into the trachea by depression of the pushbutton 78 by the same hand of the operator which is holding and manipulating the instrument. The depression of the button 78 energizes the motor 63 rotating its shaft 65 and the attached toothed cogwheel 50 while the button is depressed. The sharp teeth 51 of the wheel 50 sequentially engage the soft tube 40 at its proximal end moving it forwardly of the blade 31 and beyond the tip 32 into engagement within the trachea. At this stage, the operator need only hold the tube 40 in place while the blade 31 is separated therefrom by slight lateral movement as the blade is removed from the patient. As is conventional, the balloon seal 42 may be inflated through conduit 43 to complete the intubation.

It will be appreciated that the foregoing illustration is for illustrative purposes only, it being understood that variations in both the method and the apparatus within the scope and spirit of the invention will be apparent to those skilled in the art. For example, the shape of the blade will vary as required by particular applications and dictated by patient anatomy; the type of "quick-connect" assembly may be varied as well as the details of the power and drive mechanisms to accommodate economic and manufacturing considerations, etc. Accordingly the scope of the invention is not intended to be limited except as set forth in the appended claims.

I claim:

1. An intubating instrument comprising:
   (a) a laryngoscopic blade having a rounded distal end adapted for introduction into a patient's throat to expose the laryngeal opening for endotracheal intubation;
   (b) side wall means formed integrally with said blade and forming an elongated channel means for an endotracheal tube;
   (c) said channel means being adapted to retain said tube within said laryngoscopic blade during insertion and manipulation of the instrument and to accommodate forward displacement of said tube beyond said distal end;
   (d) said blade having a proximal end having a first quick-connect means associated therewith;
   (e) support handle housing means for supporting said blade;
   (f) second quick-connect means matable with said first quick-connect means disposed at lowermost portion of said support handle housing means;
   (g) said first and second quick-connect means being adapted to be mechanically engaged to lock said blade to said handle housing means in a predetermined angular relationship;
   (h) endotracheal tube drive means mounted in said handle housing means;
   (i) tube engaging means operatively associated with said handle housing means and said blade means and adapted to engage a proximal portion of an endotracheal tube in said channel means and to advance said tube beyond the distal end of said blade to introduce the distal end of said tube into the trachea;
   (j) finger-activated trigger means mounted on said handle housing means and adapted to initiate operation of said drive means;
   (k) whereby the exposure of the glottic opening and the introduction of said endotracheal tube may be effected with one hand while holding the handle housing means.

2. The intubating instrument of claim 1 in which:
   (a) a high intensity light is mounted on said blade proximate to said distal end;
   (b) a DC energy source for said light is included in said housing means;
   (c) circuit conductor means carried by said blade and said housing connect said light and said DC source.

3. The intubating instrument of claim 1 in which:
   (a) said tube engaging means includes a series of teeth for sequentially engaging and displacing said endotracheal tube.

4. The intubating instrument of claim 3 in which:
   (a) said trigger means is push-button actuatable.

5. The intubating instrument of claim 1 in which:
   (a) said blade is joined to said handle housing means in generally perpendicular relation thereto.

6. The intubating instrument of claim 1 in which:
   (a) said blade and said side wall means are generally semicircular in cross-sectional configuration and are adapted to accommodate all types of endotracheal tubes.

7. A method of endotracheal intubation comprising the steps of:
   (a) slidably removably associating an endotracheal tube with a laryngoscopic blade;
   (b) providing a mechanized drive means for engaging and pushing said tube through the blade;
   (c) placing the tip of said laryngoscopic blade at a patient's laryngeal opening while holding the support handle in one hand;
   (d) providing a self-contained selectively actuatable motor source means for said drive means in a support handle for said blade;

(e) while grasping said handle with said one hand and visualizing the larynx, simultaneously activating said drive source with said hand to displace said tube with respect to said blade;

(f) whereby a patient may be intubated utilizing a single hand to hold the laryngoscopic blade and to advance an endotracheal tube, leaving the other hand free for manipulation or other engagement of the patient.

8. A compact intubating instrument comprising:
(a) a laryngoscopic blade means;
(b) endotracheal tube retaining means associated with said blade means and adapted to retain and to guide a tube with respect to said blade means;
(c) a handle housing means adapted to be grasped and manipulated in one hand and to support said blade means;
(d) tube driving means disposed within said support handle housing means and adapted to engage external proximal surfaces of an endotracheal tube;
(e) activating means for driving means disposed on said handle housing means and adapted to be selectively engaged by a finger of the same hand which holds said handle housing means;
(f) whereby said tube may be driven through external proximal surfaces thereof along said blade means by an operator utilizing one hand leaving the other hand free for other manipulation of the anatomy of a patient being intubated.

9. the instrument of claim 8 in which:
(a) said drive means includes mechanism adapted to engage said tube with a series of teeth.

* * * * *